United States Patent
Daul et al.

(10) Patent No.: US 7,375,806 B2
(45) Date of Patent: May 20, 2008

(54) METHOD FOR INSPECTING THE QUALITY CRITERIA OF FLAT TEXTILE STRUCTURES EMBODIED IN A MULTI-LAYER FORM ACCORDING TO A CONTOUR

(75) Inventors: Robert Daul, Regensburg (DE); Jörg Ruschulte, Rickenbach (DE)

(73) Assignee: BST Safety Textiles GmbH, Maulburg (DE)

( * ) Notice: Subject to any disclaimer, the term of this patent is extended or adjusted under 35 U.S.C. 154(b) by 0 days.

(21) Appl. No.: 10/551,269

(22) PCT Filed: Mar. 26, 2004

(86) PCT No.: PCT/EP2004/003243

§ 371 (c)(1),
(2), (4) Date: Nov. 27, 2006

(87) PCT Pub. No.: WO2004/086013

PCT Pub. Date: Oct. 7, 2004

(65) Prior Publication Data

US 2007/0115462 A1 May 24, 2007

(30) Foreign Application Priority Data

Mar. 27, 2003 (DE) .............................. 103 13 983
Sep. 8, 2003 (DE) .............................. 103 41 318

(51) Int. Cl.
*G01N 21/00* (2006.01)

(52) U.S. Cl. .............................. 356/238.1; 236/238.2; 236/238.3

(58) Field of Classification Search .......... 28/100–171; 356/237.1–241.6, 242.1; 442/181–319
See application file for complete search history.

(56) References Cited

U.S. PATENT DOCUMENTS 4,075,498 A * 2/1978 Takasuka et al. ...... 250/559.06
4,619,527 A * 10/1986 Leuenberger et al. .... 356/238.1

(Continued)

FOREIGN PATENT DOCUMENTS

DE 32 34 608 A1 3/1984

(Continued)

*Primary Examiner*—Layla G. Lauchman
*Assistant Examiner*—Jarreas Underwood
(74) *Attorney, Agent, or Firm*—Merchant & Gould P.C.

(57) ABSTRACT

The invention relates to a method for inspecting quality criteria of flat textile structures embodied in a multi-layer form according to a contour, in particular woven, stitched, knitted, sewn or non-woven finished structures, preferably provided with cut areas or holes, separated or forming a material web, in particular when said structures are used for producing airbags. The inventive method is carried out using image-forming inspection means, in particular optical inspection means, preferably a linear array camera or CCD array camera, whereby a relative motion is produced between the structures to be inspected and the camera, and the structure is arranged at least by area at a defined distance from the image-forming inspection means, preferably on the substantially flat surface of a control table or inspection line.

The texture of the structure is analyzed according to a segmentation method. Characteristics such as center of gravity, area, main axes, etc. are calculated for individual coherent segments of the same texture, on the basis of which a distinctive system of coordinates for the structure and corresponding structures of the same type is defined which is invariant with respect to the torsion, reflection, stretch/compression and the deformation of the structure and allows measuring points to be defined. In the determining of said system of coordinates, in addition to said segment characteristics, the position and the direction of identification threads having been intentionally introduced into the structure can also be taken into account. The dimensional accuracy of the respective distances is controlled and a quality report is produced on the basis of the measuring points recorded by the system based on the quality requirements of a manufacturer or consumer, preferably in critical distance and marginal areas.

10 Claims, 9 Drawing Sheets

U.S. PATENT DOCUMENTS 6,728,593 B2 * 4/2004 Hu et al. .................... 700/143
6,735,745 B2 * 5/2004 Sarig ............................. 716/4
6,753,965 B2 * 6/2004 Kumar et al. ............... 356/431

FOREIGN PATENT DOCUMENTS

| | | |
|---|---|---|
| DE | 43 35 121 A1 | 5/1995 |
| DE | 196 32 478 A1 | 2/1998 |
| EP | 0 696 733 A1 | 2/1996 |
| EP | 0 816 554 A1 | 1/1998 |
| EP | 0 837 322 A2 | 4/1998 |
| EP | 0 889 320 A2 | 1/1999 |

* cited by examiner

METHOD FOR INSPECTING THE QUALITY CRITERIA OF FLAT TEXTILE STRUCTURES EMBODIED IN A MULTI-LAYER FORM ACCORDING TO A CONTOUR

DESCRIPTION

The invention relates to a method for inspecting quality criteria of flat textile structures embodied in a multi-layer form according to a contour, in particular when said structures are used for airbags. The inventive method is carried out with the aid of image-forming inspection means, in particular optical inspection means, preferably a linear array camera or CCD array camera, whereby a relative motion is produced between the structures to be inspected and the camera, and the structure is arranged at least by area at a defined distance from the image-forming inspection means, preferably on the substantially flat surface of an inspection table or inspection line.

An automatic inspection of textile webs is known from DE 36 39 636 A1. The plane fabric web is inspected therein using a parallel arrangement of color-area cameras, whereby the inspection is based on a color-defect recognition performed in real time simultaneously to a local structural-defect recognition performed in real time.

The structural-defect analysis uses a cyclically-specified transient image memory for a more exact two-dimensional gray-value assessment when indistinct defects are recognized within the local region. The amount of data associated with performing such an inspection is considerable, such that it is not so easily possible under industrial conditions of very short cycle times to perform inspections of quality criteria on structures having application-contingent cut areas or edges which are not permitted to fall below a certain minimum distance from a woven, stitched or sewn edge.

The process and related device for correcting draft according to EP 0 816 554 A1 refers to analyzing whether a textile web printed with a pattern or otherwise having an optically-recognizable pattern exhibits a draft in order to subsequently perform a straightening of the pattern as necessary.

To do so, the suggestion is made of capturing the pattern distinguishable on the textile web using a picture detection apparatus. The picture signals generated are then fed to a picture processing device, whereby draft detection follows just from the picture signals of one or several images of the textile web, for example by evaluating linear elements, edges and/or color limits, and that without a prior input of sample data being necessary.

While such a solution can indeed detect draft in longer textile webs with enough accuracy to subsequently drive a straightening mechanism, it is not possible to evaluate an individual object which has already been subjected to various different processing steps as to specific quality criteria in consequence of the processing steps, since the position of individual objects on an inspection table is in fact not comparable to a textile web running more or less continuously.

During the manufacturing process, the dimensioning to contoured multi-layered woven airbags is inspected a number of times; i.e., the planar extension of the incorporated contours is determined at defined locations and inspected for adherence to the respective tolerance specification. In the state of the art, this control is only performed manually and therefore takes a great deal of time, personnel and expense. In addition, the reliability of human-performed visual controls will fluctuate in each case based on the changing physical or psychological constitution of any given person responsible for the control. These types of textile products, e.g. for the production of airbags, can exhibit dimensional fluctuations, with the consequence of hindering an error-free cut. This because the known control programs for cutting airbags are not oriented to the contour, but rather to markings correlated to the contour. In such cases, there is a risk of tolerance specifications not being heeded and it will not be possible to use the final products resulting therefrom as actually intended.

In light of the above, it is therefore the task of the invention to provide an improved method for inspecting quality criteria, in particular of flat woven, stitched, knitted, sewn or non-woven textile structures embodied in a multi-layer form according to a contour having cut areas or holes such that the method in particular also allows an analysis of individual structures having completely different contours and which are also essentially only imprecisely aligned on an inspection table without an otherwise complex procedure needed to define an initial position, e.g. by manual positioning the structure to be inspected at an edge of the inspection table.

The solution to the inventive task is solved with the method defined in accordance with claim 1, with the subclaims representing no less than advantageous embodiments and developments.

The inventive method for inspecting the quality criteria of flat woven or sewn textile structures embodied in a multi-layer form according to a contour having cut areas or holes, in particular individual structures to be used in turn especially for airbags, draws on known image-forming inspection means, e.g. one or more linear array cameras or CCD array cameras. Ultrasonic sensors, sonars or radar devices can, for example, be used as the image-forming inspection means, whereby radiation in the visible as well as non-visible range, e.g. x-ray, can be used for the optical inspection means.

A relative motion is furthermore generated between the structure(s) to be inspected and the camera in that the structure is positioned at a defined distance on a substantially flat surface of an inspection table or inspection line or is led past the camera's field of view at a defined distance by a roller.

In a first step, an initial image is taken of the e.g. textile airbag, followed by the captured image data being saved. Depending upon the respective textile material, different types of illumination can be used to record the image, e.g. incident light or transmitted light. The image recording device is configured accordingly.

In a next step, an image data correction can advantageously be made such that the resolution ratio of the X-direction to the Y-direction results in 1.

Because of the different textures involved, which are likewise depicted differently in the image, e.g. with different brightnesses, segmented and per each segment, e.g. total structure, holes, etc., the pre-processed image data will define characteristics such as e.g. area, center of gravity, localized rectangles, center axes and the like. A segment here refers to one coherent area having uniform texture.

From the position of the segment's centers of gravity to one another and the other characteristics as returned, the textile structure's torsion, reflection, stretching or compression, deformation, etc. is determined using standard comparative basis data which was previously acquired in like fashion from an image taken of a target textile structure.

The directional positioning and/or angle of individual specially-colored identification warp and weft threads allows for the ensuring of an additional determination of the deformation to the textile structure.

From these acquired characteristics, a distinctive system of coordinates can be determined for the textile structure, e.g. with point of origin at the center of gravity of the cut textile structure, X-axis in the weft thread—or first main axis direction, Y-axis in the warp thread—or second main axis direction, whereby this system of coordinates is then used for the further measurement or control tasks.

Subsequently, measuring points are specified, preferably in critical distance and marginal areas, using manufacturer or consumer quality specifications. Such measuring points can, however, also be taken and updated from a learning algorithm.

Especially when there turns out to be no risk of certain cut areas or marginal regions falling short in terms of distance and/or dimension, a measurement scatter diagram can be defined in order to improve the reliability of the declared quality for such critical areas.

All conceivable distances between the individual texture borders, an image's segment borders respectively, as determined by the system of coordinates described above can be measured. Tolerance limits can be defined for each measuring point. The measurement data itself can moreover be recorded in a quality log and/or used to extract the textile structure for further treatment or distribution based on an accept/reject assessment principle.

When an undefined position is detected for the textile on the inspection table, in particular a certain area of stretch or compression to the textile structure, the inventive configuration allows for analyzing whether and to what extent there are measuring points for determining critical distances in the stretched and/or compressed area. If there are, predefined measuring points can be rejected and the possibility then arises of defining alternative measuring points. If there turns out to also be alternative measuring points in the stretched and/or compressed area, this would then occasion recording another image after repositioning the textile structure on the inspection table.

Recording the image is done in a procedure using either transmitted or incident light. In connection hereto, the inspection table or the inspection line is configured as an x-ray mechanism or the surface of the inspection table or the inspection line creates a contrasting background for the textile structure. Thus, sufficient contrast between structure and rear/background is created. Provision for both types of illumination can be made in the design such that retrofitting does not become necessary.

An advantageous variation of the procedure records the image by means of scanning so that while the image data is being scanned, the segmenting algorithm is already being performed on the partial image becoming available.

Analysis of the textile structure's dimensional accuracy can be realized such that different formational structures are imaged in differing contrast to one another and at least one continuous measurement line of a formational structure is added to the imaged formational structure, whereby at least one distance is measured between at least two measuring points situated on the measurement line and defined by a change in contrast. The textile structures are thus analyzed as to their location and position to one another at points appropriate thereto.

For example, a determination of textile structure contour can be performed such that at least one contour-defining measuring point can be set on at least one measurement line disposed on a determined contrasting structure and an aggregate of measurement lines can form a contour line with the associated measuring points. This contour line can then subsequently serve for controlling the movements of further processing mechanisms, in particular cutting or sewing devices.

The invention will be described in greater detail below with reference being made to an embodiment as well as figures. The same reference numerals will be used for similar components or process steps or components and process steps having similar effect. Shown are:

FIG. 1 a view of an embodiment of a scanner for recording images from a textile structure, FIG. 1a a total view of an embodiment of a curtain side airbag exhibiting a resolution ratio equalized in the X and Y directions, FIG. 2 a total view of an embodiment of a background-segmented image of the curtain side airbag, FIG. 3 a total view of an embodiment of the segmented image of the curtain side airbag with examples of the center of gravity position for holes in relation to the position of the center of gravity for the overall image, FIG. 4a-c representations of an embodiment for the scanning process within the scope of the segmentation process, FIG. 5a representations of an embodiment in various different filter modes in comparison to an original section, FIG. 5b illustration of a filter embodiment for a web contour of the curtain airbag as a closed area, FIG. 6 illustration of a filter embodiment for a web contour of the curtain airbag as an image of the edges, FIG. 7a representation of an embodiment of a principle for detecting identification threads, FIG. 7b representation of an embodiment for calculating center of gravity and determining an object-coordinate system for the curtain airbag, FIG. 7c representation of an embodiment of the functioning of a series of measurement filters, FIG. 8 an illustrative example of the principle of calculating the dimensions for structures of the curtain airbag, FIG. 9a, b representations of embodiments for a contour analysis of a cut airbag, FIG. 10 embodiment of a contour determination for cutting an airbag.

The embodiment as shown in accordance with FIGS. 1-10 illustrates the final inspection performed on an airbag.

The embodiment shows, situated on an inspection table, a textile structure of a curtain side airbag of defined dimensions having technically-contingent marginal structures as well as cut areas in the form of unilateral elongated holes. In order to ensure the following description yields a clear and concise representation, the terms "curtain side airbag" and "airbag" will be used synonymously, whereby the person skilled in the art can appreciate that the method hereby presented is neither limited to the manufacturing process for curtain side airbags nor to the production process for airbags in general.

Said embodiment has the task of analyzing whether the cut sections/holes have a defined position and whether the distances as well as the position of the holes have a defined value relative the stitched or sewn edge of the airbag material. Moreover, the dimensional accuracy to the cut section of the airbag is to be controlled.

Figure 1:
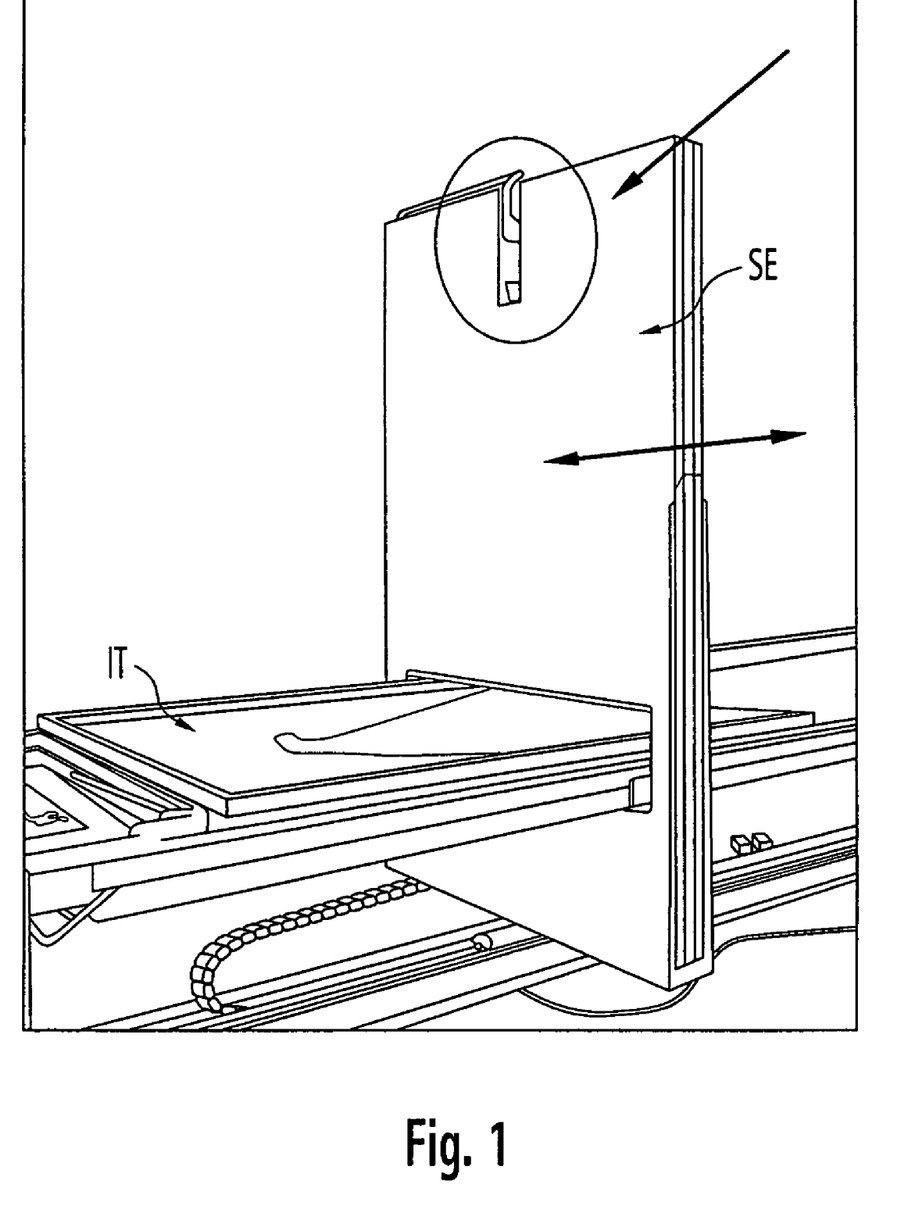

In accordance with FIG. 1, the airbag is first positioned on table IT such that it can be recorded by a camera system. It is illuminated from below by means of transmitted light or from above by means of incident light. The various different optical characteristics exhibited in the web/cut contours in contrast to the incidence or passage of light can thus be defined as a representation and recorded.

In an advantageous embodiment, table IT additionally has a glass plate as its supporting surface.

A scanner SE, consisting of a CCD array camera and on-off illuminating means, is fixed to table IT, arranged above the table plate in the case of incident light and below the table plate in the case of transmitted light. Said scanner SE realizes a relative motion respective table IT. This motion is indicated in FIG. 1 by a white double arrow. The motion of scanner SE over the airbag to be inspected is analogous to the movement of known flatbed scanners, whereby so doing results in an image of the airbag being recorded. The image is then available subsequent the scanning process as a gray-tone or color image.

Figure 1A:
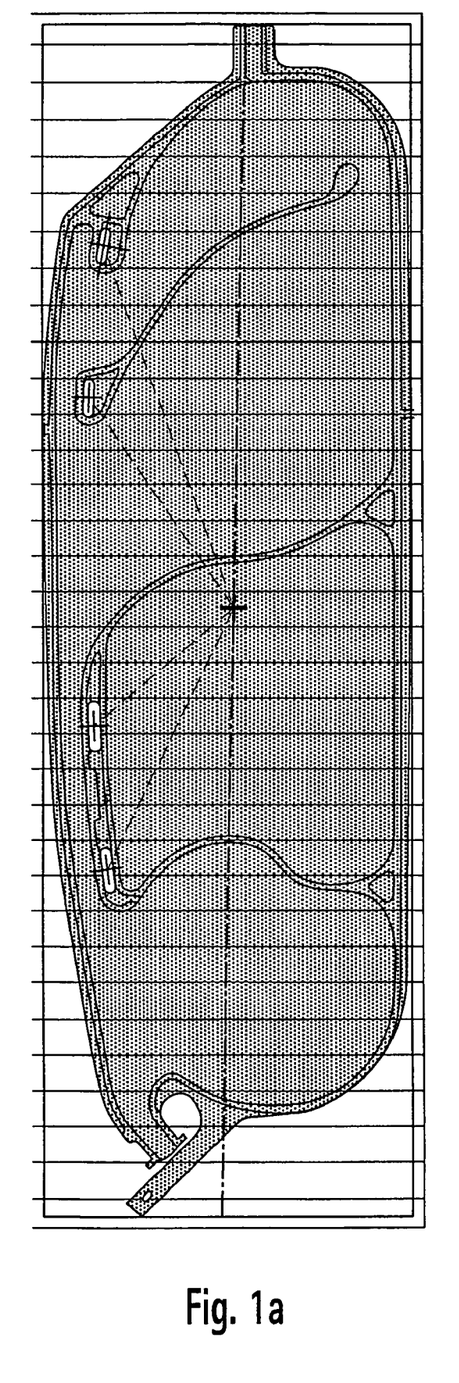

The image thus captured and shown as an example in FIG. 1a is then subsequently filtered in different ways for further processing and thus optimized for further use. Two basic filter procedures can essentially be used hereto.

Figure 2:
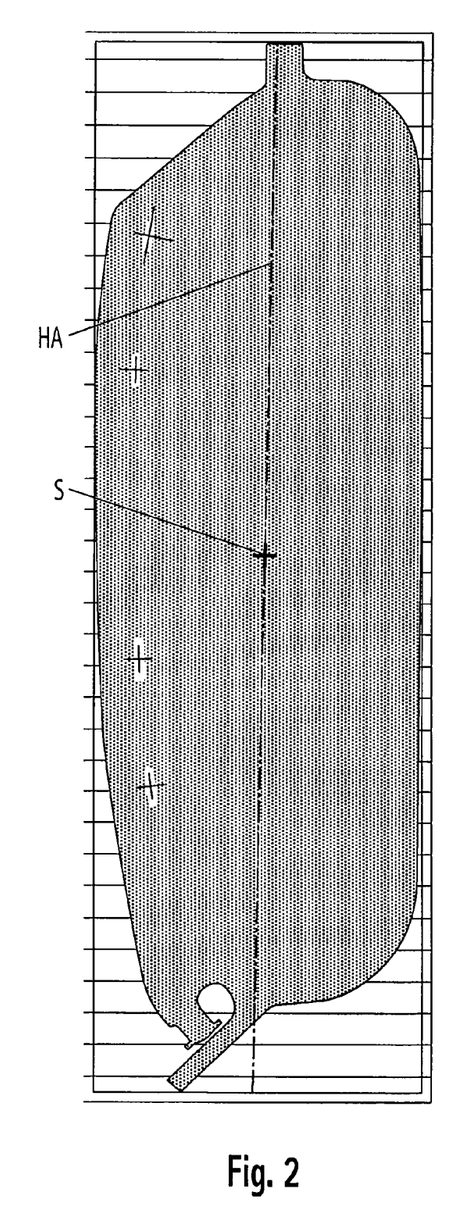

A first filter procedure is shown in FIG. 2. Here the cut airbag appears as a black segment surrounded by a white background. In this procedure, the binarization of the segmentation threshold must be set such that the entire area is recognized as one coherent structure. The black pixels represent a geometrical area for which different characteristics can be calculated such as, for example, area (number of black pixels), center of gravity S, main axis HA and others as in accordance with FIG. 2

The cut areas or holes contained within the black segment as white segments can likewise be considered as coherent geometrical areas having the same characteristics of area, center of gravity, main axis, etc. (see FIG. 3).

Figure 3:
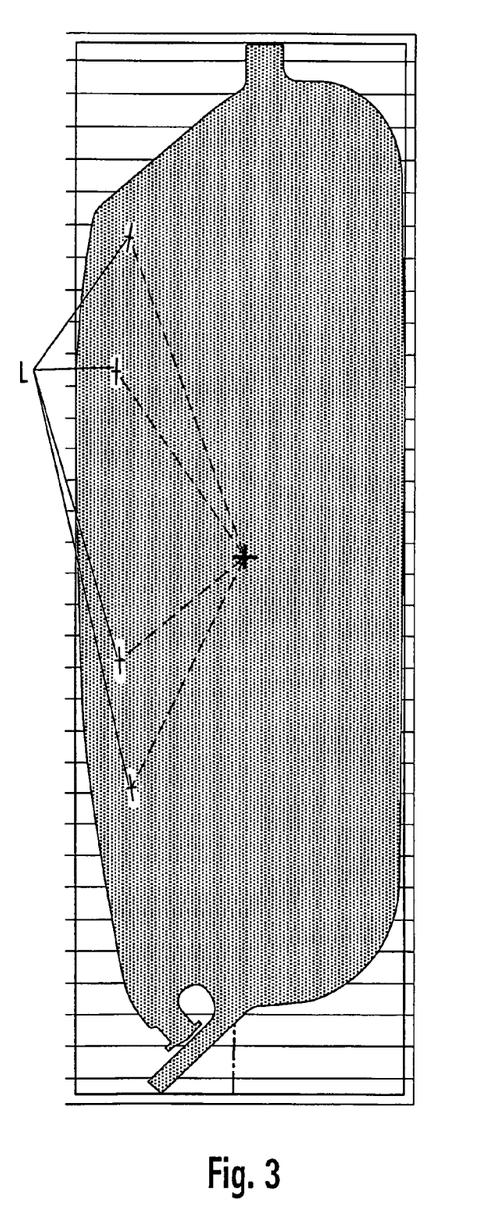

The torsional/reflective direction as well as any compression or stretch or deformation to the textile structure can be calculated from the position of the centers of gravity and main axes, i.e. the determined characteristics of the individual segments as a whole and relative one another (FIGS. 2 and 3).

In order to make a selection and differentiate between relevant and irrelevant segments, limiting values are included as characteristics to be determined such as, for example, minimum and maximum area, minimum and maximum X-elongation, etc.

Figure 4A:
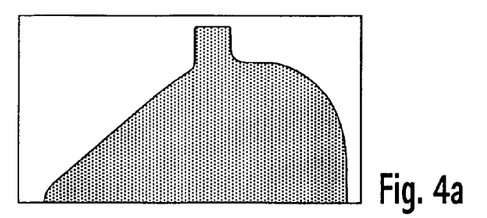
Figure 4B:
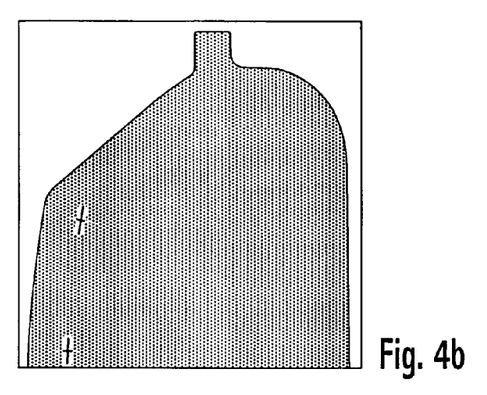
Figure 4C:
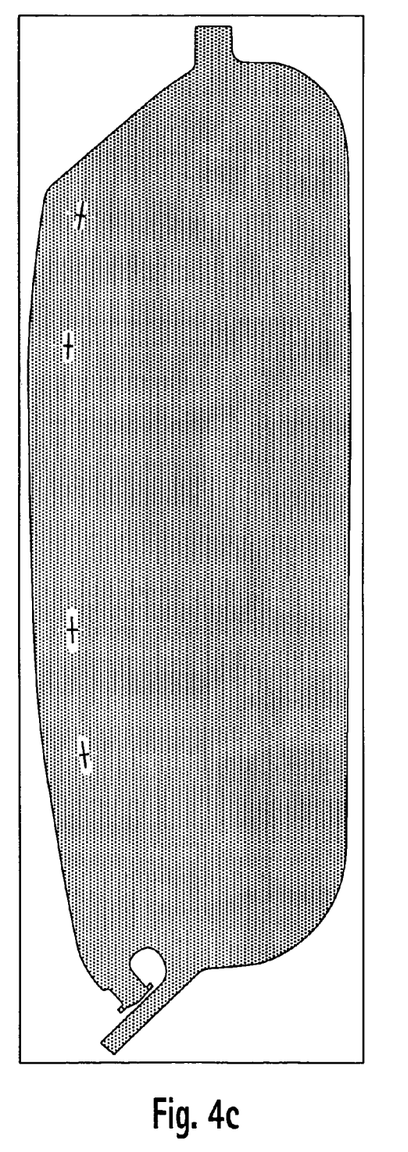

As FIGS. 4a-4c show, the first analytical step, i.e. segmentation, is already being performed as the image is being recorded.

In order to attain a distinctive system of coordinates for the specific type of airbag, the airbag segment's center of gravity and main axes are used (FIG. 2)—the second main axis is perpendicular to the first and is therefore not shown in the figure—so that the airbag segment's center of gravity corresponds to the point of origin, the two main axes of the coordinate axes. The reflective direction can be readily determined by depicting the centers of gravity for holes L in this coordinate system (see FIG. 3).

By specifying the maximum elongation of the airbag segment toward these coordinate axes, a distinctive benchmark for the airbag can additionally be defined.

The coordinate system can be further adapted relative deformation from the exact position of the centers of gravity for the holes within the airbag segment.

Figure 5A:
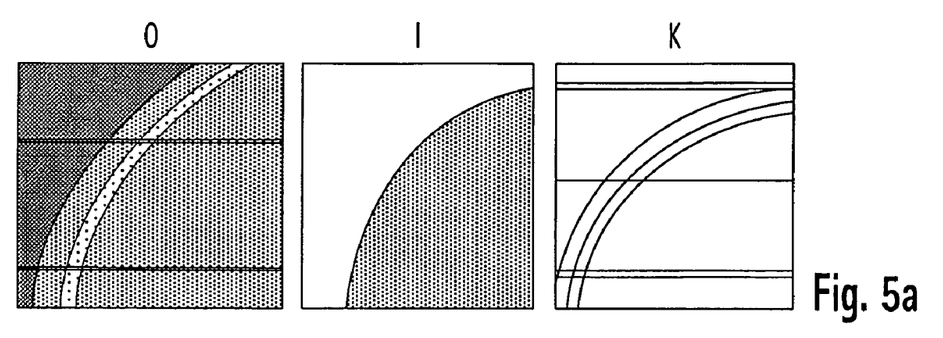
Figure 5B:
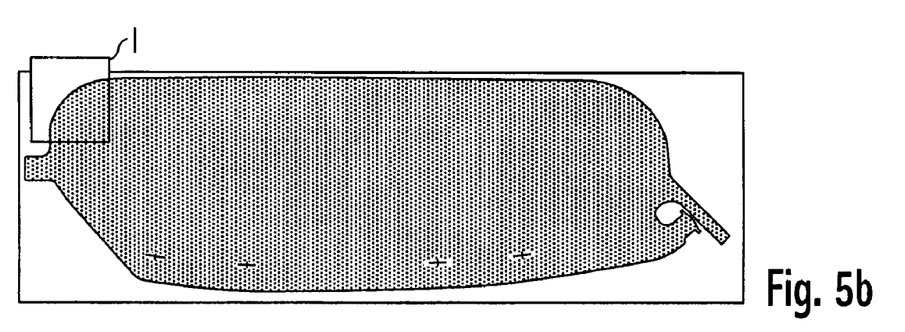
Figure 6:
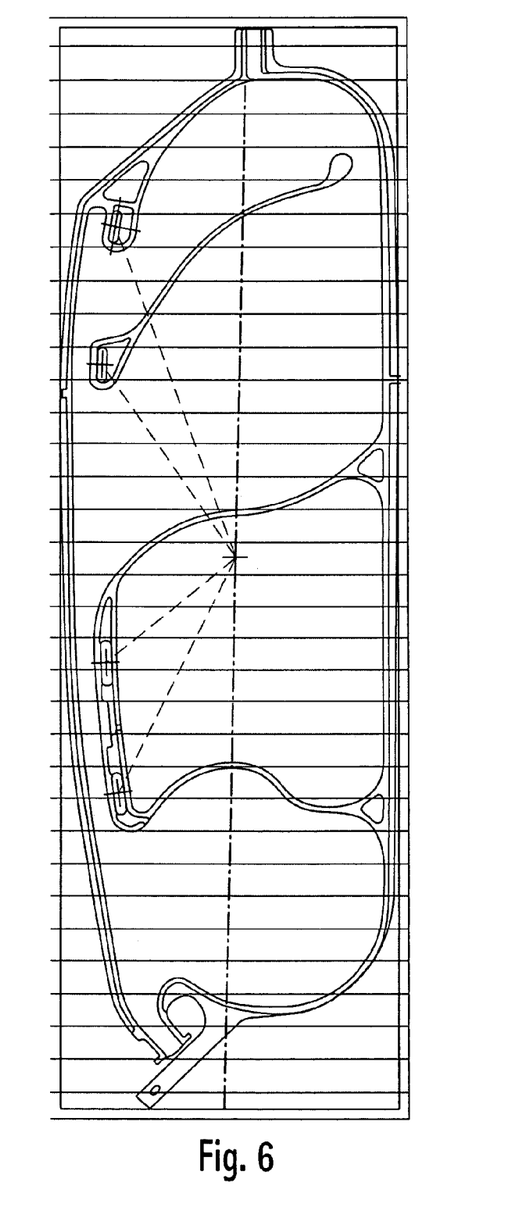

As can be seen from the FIG. 5a section representations, original image O depicted on the left can be converted into both the segment image I as well as into an image of the edges K by the described as well as other segmenting procedures or also by means of suitable image filters. In this context, FIG. 5b again shows the full image associated with segment image I, FIG. 6 shows an image of the edges in the embodiment of a total view.

Figure 7A:
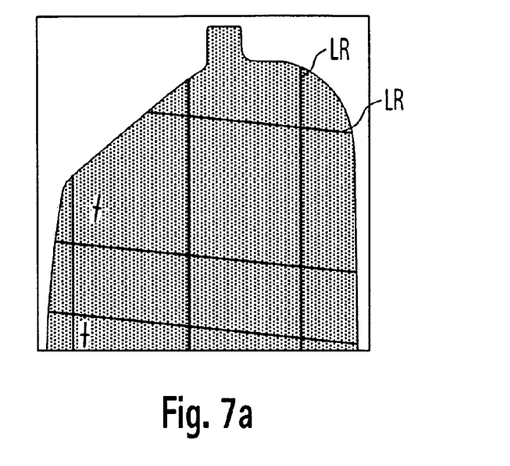

The possibility for determining a draft in the textile surface of the structure, in particular of the airbag, in which above all the warp and weft threads are not at right angles to one another, will be described in the following with reference being made to FIG. 7a. Here, the actual angle between the warp and weft threads is determined in order to be able to subsequently perform the necessary draft-related work on the web structure.

In this embodiment, differently-colored, contrast-producing threads which had been woven into the structure's textile fabric are detected. These are shown in the FIG. 7a representation as a raster LR of identification threads. These identification threads then exhibit the same draft as the warp and weft threads of the entire material. An edge detection filter is advantageously used in detecting the identification threads.

Figure 7B:
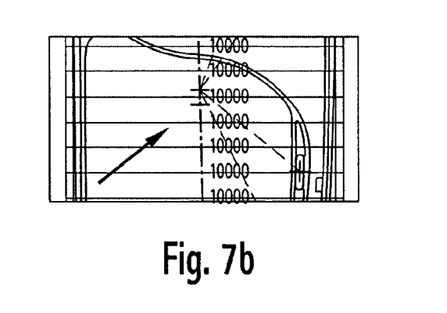

In a next step, and in accordance with FIG. 7b, the center of gravity of the structure is calculated and same is defined as the point of origin for the structure in the reference system. The system of coordinates is then warped and/or deformed in respect of the draft determined in the preceding step. The X-axis of the structure's reference system, the airbag respectively, is then aligned along the weft threads and the Y-axis along the warp threads. The actual position of the holes in this coordinate system is what defines the position of the structure, in particular the airbag. Given an asymmetrical form to the structure or an asymmetrical position of the holes, concerted work or action can then always be performed at the relevant location independent of the position and orientation of the structure.

Figure 7C:
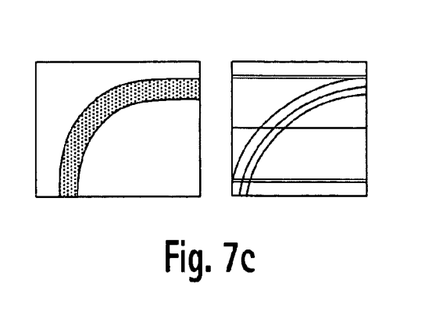

The detected structure can now be prepared in further filter steps; an example hereto is illustrated in FIG. 7c.

Figure 8:
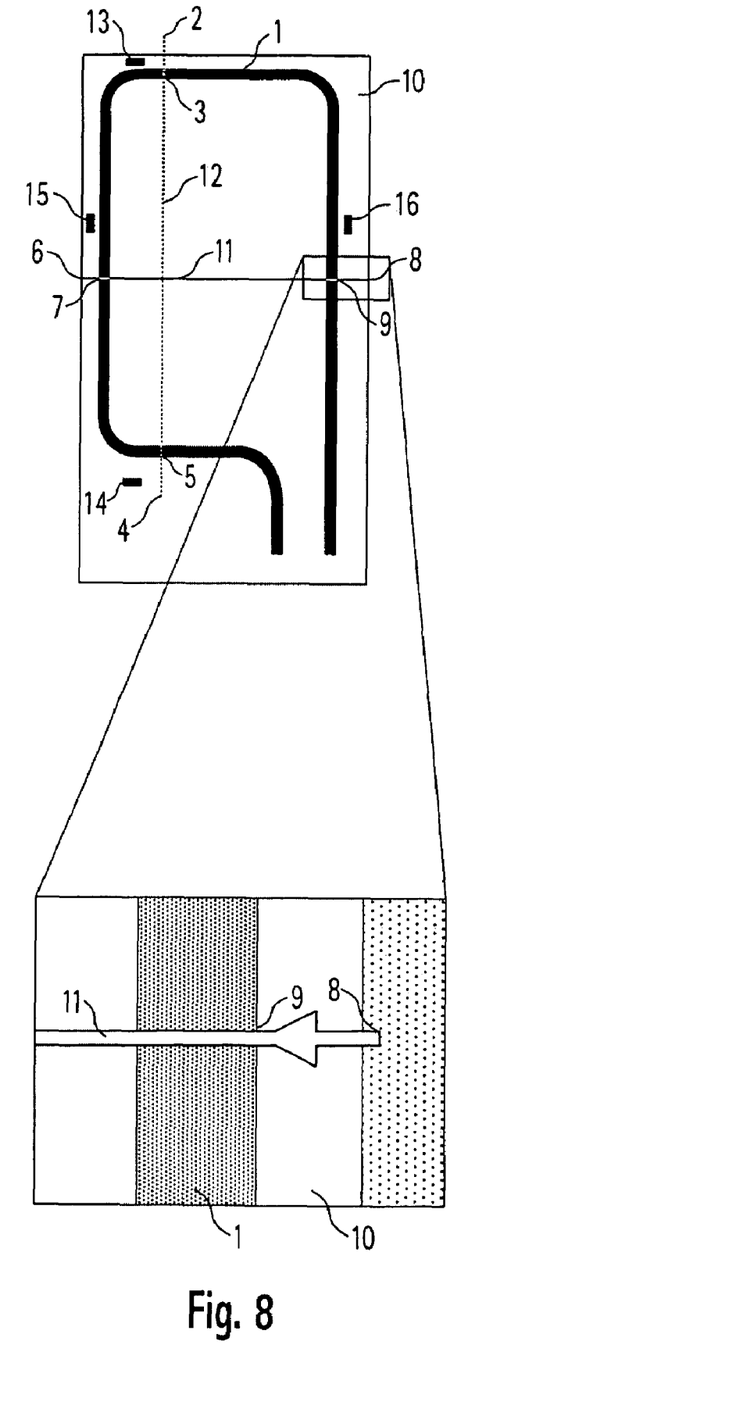

In accordance with the embodiment of FIG. 8, a dimensional determination is made on an airbag in a material web under the described circumstances as follows. First, an individual airbag is determined in the material web as described above. The measuring filters prepare the image of the airbag such that a double-layer area 10 is depicted in white and a single-layer area 1, which can for example be the area of a seam, is depicted in black. Measurement lines 11 and 12 with terminuses 2, 4, 6, 8 are positioned atop these depicted contours which are in double-layer area 10. An analysis is then made along measurement lines 11 and 12 beginning at terminuses 2, 4, 6, 8 and proceeding toward the center as to when a change in color from white to black occurs. Seam area 1 is thus localized at these locations. In the FIG. 8 example, this is the case with points 3, 5, 7 and 9. The respective distance between each of the points 7 and 9, respectively 3 and 5, is then measured along measurement lines 11 and 12.

Reference points 13 to 16 can furthermore be designated for the airbag structure right from the start, from which the measurements for the airbag dimensions can be taken. By processing the image through the measuring filters, it then becomes possible to make these invisible. Hereto, using measurement lines 11 and 12, distances to more pronounced proximate contours, for example to 1, can likewise be determined. Subsequently, the measurement associated with the reference points can be established using correction values, correction factors and other such similar parameters. This example in principle also allows for detecting a color change from black to white.

Figure 9A:
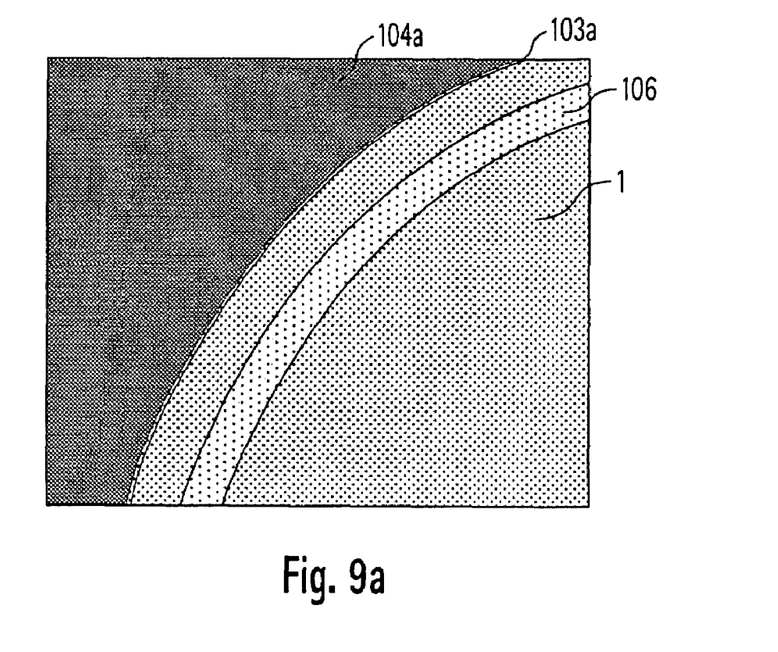
Figure 9B:
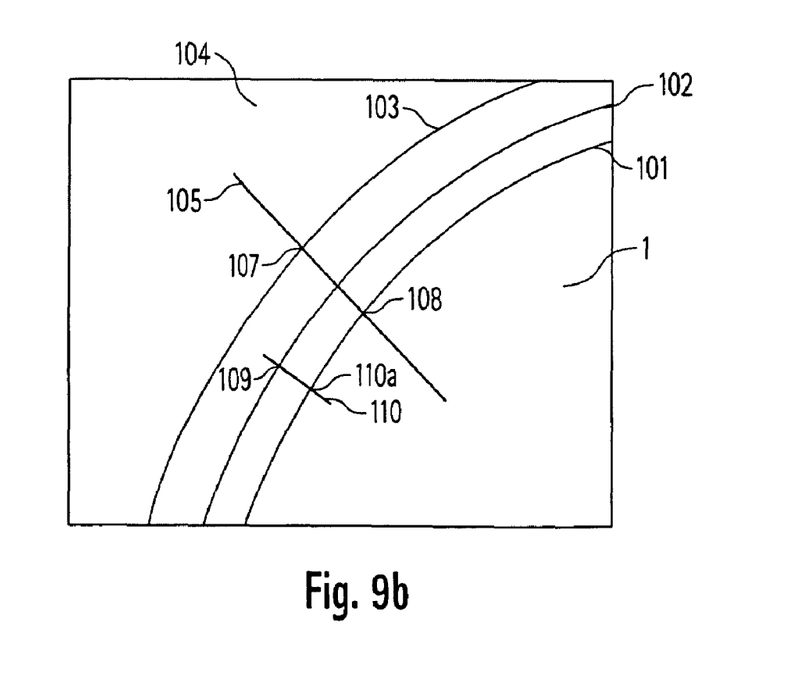

An embodiment for inspecting the contour of a cut airbag will now be described on the basis of FIG. 9a in conjunction with FIG. 9b. The contour of the airbag is determined by means of the previously-described steps. The measuring filters then prepare the image captured of the airbag such that the transitions, for example between a line of intersection 103a and the background of the airbag and the line of intersection 106 between single-layer and double-layer area 1, are depicted as lines 101, 102, 103. Measurement lines 105, 110 are thereafter positioned atop lines 101, 102 and 103 representing the transitions and the distances between points 108 or 109 and 110a are determined along measurement lines 105 and 110 in accordance with the procedure as just described.

These values can now be analyzed as to their dimensional accuracy and ranges of tolerance. Airbags exhibiting measured contours or dimensions which do not correspond to specification can thus be detected and separated.

Figure 10:
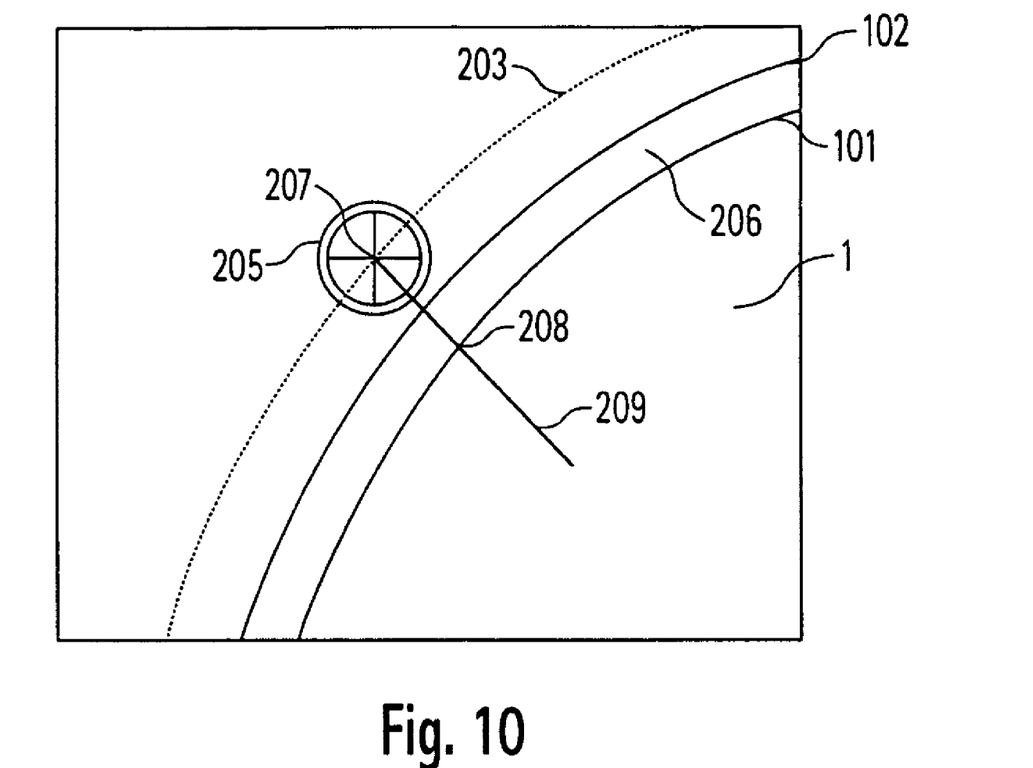

An embodiment of a contour determination for the cutting of an airbag will now be described in connection with FIG. 10. The respective individual airbag is detected in the material web as in the steps described above. The measuring filters then prepare the image of the airbag such that the transitions, for example between the single-layer and double-layer areas 206, are represented as lines 101, 102. Measurement line 209 is now positioned atop lines 101 and 102 representing the transitions. Using the same method as described above, point 208 is now determined on one side along measurement line 209. Point 207 is then determined from a fixed distance to point 208 along measurement line 209. On the basis of all points 207 on all measurement lines, a path 203 is specified for cutting means to cut the airbag.

REFERENCE NUMERAL LIST

HA main axis
S center of gravity
L holes
O original section
I segment section
K edge image section
LR identification thread raster
1 single-layer area
2 measurement line terminus
4 measurement line terminus
5 color change point
6 measurement line terminus
7 color change point
9 measurement line terminus
10 double-layer area
11 measurement line
12 measurement line
13 reference point
16 reference point
101 line of transition
102 line of transition
103 line of transition
103a line of intersection
105 measurement line
106 line of intersection
108 measuring point
109 measuring point
110 measurement line
110a measuring point
206 double-layer area
207 point
208 point
209 measurement line

The invention claimed is:

1. Method for inspecting the quality criteria of flat textile structures embodied in a multi-layer form according to a contour, in particular woven, stitched, knitted, sewn or non-woven finished structures, including cut areas or holes, separated or forming a material web, said structures being used for airbags, carried out using image-forming inspection means, in particular optical inspection means, including a CCD array camera or a linear array camera, wherein a relative motion is produced between the structures to be inspected and the camera, and the structure is arranged at least by area at a defined distance from the image-forming inspection means preferably on a substantially flat surface of a control table or inspection line or led past the field of view of the camera at a defined distance by a roller, comprising the following steps:

recording the structure using the camera, and saving or buffering the image data captured;

segmenting the image data captured based on the texture differences distinguishable in the image;

determining segment characteristics for the individual image segments such as segment center of gravity-segment area-segment main axis and/or localized rectangles or the like, on the basis of which a distinctive system of coordinates for the structure and corresponding structures of the same type can be defined which is invariant relative the torsion, reflection, stretching, compression and deformation of the structure, said system of coordinates allowing a definition of measuring points to be made.

2. Method according to claim 1, wherein the definition or specification of measuring points is realized based on manufacturer or consumer quality specifications.

3. Method according to claim 1 wherein the inspection is made of the actual dimensional accuracy and pre-defined distances from cut areas to seams or from seams to the outer edge of the structure.

4. Method according to claim 1, wherein a quality log is produced on the basis of the determined inspection data.

5. Method according to claim 1, wherein optically detecting the position and/or direction of identification threads woven into the structure to be inspected is used in the determination of the distinctive system of coordinates.

6. Method according to claim 1, wherein image processing edge-scanning algorithms are used to analyze the actual dimensional accuracy of distances adjacent the segment borders.

7. Method according to claim 1, wherein upon an undefined position comprising a certain area of stretch or compression to the textile structure being detected, an analysis is carried out as to whether and to what extent there are measuring points for determining critical distances in the stretched and/or compressed area in order to subsequently reject selected measuring points, define alternative measuring points, or retake the image of the relevant textile structure.

8. Method according to claim 1, wherein recording the image is a procedure using transmitted or incident light, wherein the inspection table or the inspection line is configured as an x-ray mechanism or the surface of the inspection table or the inspection line creates a contrasting background for the textile structure.

9. Method according to claim 1, wherein the textile structure is detached from the material web on the basis of a contour line ascertained in accordance with one of the afore-mentioned procedures.

10. Flat textile structures embodied in a multi-layer form according to a contour, the structure comprising woven, stitched, knitted, sewn or non-woven finished structures, used for airbags, which are detached from the material web in a procedure according to claim 9.

* * * * *